United States Patent [19]

Nummy

[11] Patent Number: 4,788,329

[45] Date of Patent: Nov. 29, 1988

[54] PREPARATION OF CYCLOHEXYL MONO- AND DIURETHANES AND ISOCYANATES DERIVED THEREFROM BY ADDITION OF METHYLCARBAMATE TO LIMONENE, PROCESS AND COMPOSITIONS

[75] Inventor: Laurence J. Nummy, Newburgh, N.Y.

[73] Assignee: American Cyanamid Company, Stamford, Conn.

[21] Appl. No.: 926,068

[22] Filed: Nov. 3, 1986

[51] Int. Cl.$^4$ .......................................... C07C 119/045
[52] U.S. Cl. .................... 560/330; 560/115; 560/345
[58] Field of Search ........................................ 560/330

[56] References Cited

U.S. PATENT DOCUMENTS 2,692,275 10/1954 Bortnick .............................. 560/345
4,510,097 4/1985 Kehr .................................... 560/330
4,618,707 10/1986 Grimm ................................. 560/337

OTHER PUBLICATIONS

Lesiak, Pol, J. Chem., 52, pp. 927–932, (1978).

Primary Examiner—Michael L. Shippen
Attorney, Agent, or Firm—Michael J. Kelly; Steven H. Flynn

[57] ABSTRACT

A process is disclosed whereby mono- and diurethane cyclohexyl derivatives are obtained corresponding to the Lewis acid-catalyzed addition reaction of dipentene and methyl carbamate at a temperature of from about 40° to about 150°C. The mono- and diurethane cyclohexyl derivatives are pyrolytically converted to other corresponding mono- and diisocyanate cyclohexyl derivatives. Novel vinyl unsaturated monoisocyanate cyclohexyl derivatives useful as reactants for polyfunctional compounds to produce cured compositions are disclosed.

2 Claims, No Drawings

PREPARATION OF CYCLOHEXYL MONO- AND DIURETHANES AND ISOCYANATES DERIVED THEREFROM BY ADDITION OF METHYLCARBAMATE TO LIMONENE, PROCESS AND COMPOSITIONS

FIELD OF THE INVENTION

The present invention relates to a novel process for the preparation of cyclohexyl mono- and diurethanes and their correspondingly derived mono- and diisocyanates, and to novel monoisocyanates produced thereby, and to curable compositions which comprise such monoisocyanates. More particularly, the invention relates to the preparation of the aforementioned compounds by the addition of methyl carbamate to limonene or dipentene in the presence of an acid to form cyclohexyl carbamate derivatives including mono- and diurethane compounds which can be cracked in hot inert solvent to give the corresponding cyclohexyl isocyanates. These cyclohexyl isocyanates comprise diisocyanates and novel monoisocyanate compounds, both of which are useful as reactants in curable resin compositions and in other plastic applications.

BACKGROUND OF THE INVENTION

Various methods have been employed to produce isocyanate compounds. It is known that diamine or monoamine derivatives can be reacted with phosgene at a temperature of about 100° C. for about 28 hours. The by-product hydrogen chloride and excess phosgene are removed by blowing nitrogen through the liquid reaction mixture and recovering the desired mono- and diisocyanates.

In another approach, Klein and Gerhard, Forsch Technol. 1983 CA 100:68763q, report that the unsaturated compound limonene can be treated with hydrogen cyanide and subsequently with phosgene to form a diisocyanate derivative, which is thermally rearranged to diamine dipentene, which in turn, can be treated with phosgene to prepare a diisocyanate of the formula

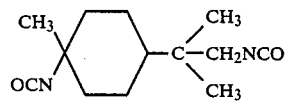

Drawbacks of this process are the toxicity of the hydrogen cyanide and phosgene, and corrosion problems associated with the by-product hydrochloric acid.

The difficulties with direct phosgenations have led to the development of non-phosgenation routes, and these generally involve the pyrolytic thermolysis or cracking of carbamic acid esters or urethanes.

It is also known that isocyanate compounds can be prepared by the reaction of corresponding olefins with isocyanic acid, by reaction of the corresponding halide with an alkali metal isocyanate, and by reaction of the corresponding halide with isocyanaic acid.

Merely by way of illustration, it has been shown in Bortnick, U.S. Pat. No. 2,692,275, that 1,8-diisocyanato-p-menthane can be prepared by pyrolyzing the corresponding carbamate in the presence of a basic catalyst such as the water-soluble metal hydroxides or alkoxides or the water-insoluble metallic oxides or hydroxides.

Mueller and Merten, Chem. Ber. 98, 1097–1110 (1965), carry out the alkylation of urethane, i.e., carbamic acid ethyl ester with a number of cyclic and noncyclic olefins in the presence of acid catalyst to form N-substituted urethanes. The N-substituted urethanes are converted to corresponding isocyanates by "transurethanation", that is, by reacting industrially available higher-boiling mono- or polyisocyanates, e.g., tolylene diisocyanates with the N-substituted urethanes at 200°14 240° C. to release isocyanates.

These various processes are disadvantageous for one or more reasons, such as that the materials are difficult to handle or are corrosive, the yields are poor, expensive reactants are required and the products are difficult to recover.

In Singh, Chang and Forgione, U.S. Pat. No. 4,439,616, tertiary aralkyl isocyanates are produced by thermal cracking of corresponding urethanes formed by the addition of corresponding olefins, e.g., diisopropenyl benzene and carbamic acid esters, e.g., methyl carbamate, at moderate temperatures and in the presence of an acid catalyst. There is no hint or suggestion in Singh et al. that wholly non-aromatic mono- and diisocyanate compounds can be produced by the addition of an olefinic substituted cycloalkene and a carbamic acid ester.

It has now been discovered that wholly non-aromatic cyclohexyl isocyanate compounds can be prepared by a new route of synthesis involving catalyzed pyrolysis of urethanes that have themselves been synthesized by the addition of alkyl carbamate, such as methyl carbamate, to the compound limonene or dipentene [1 methyl-4-(1-methylethenyl)cyclohexene].

It is an important object of this invention to produce cyclohexyl isocyanates utilizing non-corrosive, low-cost starting materials such as limonene or dipentene and methyl carbamate in a simple process yielding the desired isocyanates whereby they are readily recovered and purified.

SUMMARY OF THE INVENTION

In accordance with this invention mono- and diisocyanate cyclohexyl compounds are prepared by the addition of methylcarbamate to limonene to form mono- and diurethanes followed, if desired, by the thermal cracking of such urethanes to form the isocyanate and the free alcohol.

The present invention thus provides a process for production of urethanes of the formulae:

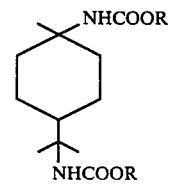 (I)

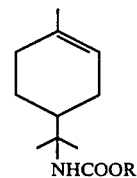 (II)

and

-continued

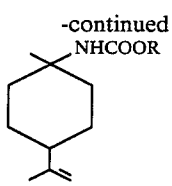  (III)

or a mixture of any of (I), (II) and (III) wherein R is alkyl of from about 1 to about 30, preferably 1 to 18, carbon atoms, by reacting (a) an unsaturated cyclic hydrocarbon of the formula

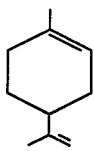

with (b) at least 2 moles per mole of (a) of (b) of carbamic acid ester of the formula

H$_2$NCOOR wherein R is as defined above, in the presence of (c) an effective catalytic amount of acid at a temperature of from about 40° to about 150° C. until formation of said urethane compounds (I), (II) or (III), or a mixture of any of them is substantially complete.

Also contemplated by this invention is a process for the production of mono- and diisocyanate cyclohexyl compounds which comprises heating the urethane product (I), (II) and (III) or a mixture of any of the foregoing at a temperature in the range of from about 200° C. to about 300° C. until formation of an isocyanate compound of the formulae:

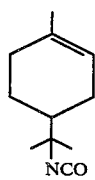  (IV)

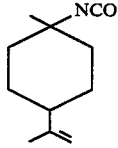  (V)

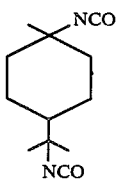  (VI)

or a mixture of any of compounds (IV), (V) and (VI) is substantially complete.

Also provided according to the present invention are compounds selected from those of the formulae:

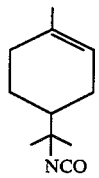  (IV)

and

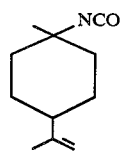  (V)

or a mixture of said compounds. These compounds can be vinyl addition polymerized or copolymerized to produce urethanes which can form curable compositions with polyhydric compounds, e.g., polyols, polyamines, and with water.

DETAILED DESCRIPTION OF THE INVENTION

The limonene or dipentene, 1-methyl-4-(1-methylethenyl)cyclohexene, useful as a starting material in accordance with this invention and represented by the formula

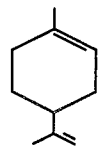

can be isolated from the ethereal oils of various natural plants including lemon, orange, caraway, dill, bergamot, and mandarin peel oil, the latter as reported by Kugler and Kovats, *Helv Chim Acta* 46, 1480 (1963).

The carbamic esters used as component (b) herein are compounds represented by the general formula:

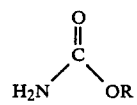

wherein R is as defined above, i.e., alkyl of from about 1 to about 30 carbon atoms, straight chain or branched. Examples of suitable alkyl carbamates are methylcarbamate, ethylcarbamate, propylcarbamate, butylcarbamate, octadecyl carbamate, 2-ethylhexylcarbamate, triacontyl carbamate, and the like. Especially preferred for use herein is the compound methylcarbamate also known as carbamic acid methyl ester.

Methyl carbamate or other carbamates can be added in stoichiometric proportions to limonene or dipentene, but preferably the carbamate is in substantial excess and functions as solvent and catalyst moderator as well as reactant. It is preferred in accordance with this invention to use from 50% to 800% stoichiometric excess of the carbamate, preferably about 300% excess of the carbamate.

The Lewis acid catalysts useful in this invention include soluble acid catalysts such as boron trifluroide etherate BF₃. Et₂O and solid acid catalysts, such as sulfonic acid, e.g., Amberlyst-15 ® available from the Rohm & Haas Company and polysulfonic acid resin, e.g., Nafion-H ® available from the Du Pont Company. Other suitable acid catalysts include sulfuric acid, toluene sulfonic acid, dodecylbenzene sulfonic acid, hydrocarbon sulfate esters, hydrochloric acid, and the like.

The amount of catalyst required to promote the addition of dipentene and carbamic acid ester is not critical and can be varied widely. Where substantial excess of carbamic acid ester is utilized the amount of catalyst, based on the diol is typically 0.01 to 10 mole % and preferably about 2 to 5 mole %.

The reaction can take place in the absence of solvent or in the presence of solvents, such as methylene chloride, toluene, xylene, chlorobenzene and so forth.

Preferably the carbamate is heated to maintain it molten, from 40° C. to 150° C. being suitable. The catalyst is mixed into the molten carbamate, and the unsaturated hydrocarbon is then slowly added. When the reaction is complete the mixture is treated to remove or neutralize the catalyst. Unreacted carbamate ester is then separated by distillation in partial vacuum or by adding a large excess of water and filtering to separate insoluble urethane products from water-soluble carbamate ester.

If excess of carbamate is employed this can also be distilled off at partial vacuum and recovered. The recovered carbamate can be recycled along with catalyst. The reaction mixture of urethanes, unreacted carbamate ester, catalyst, and byproducts can also be separated by adding a large excess of an aqueous medium, for example, sodium carbonate solution to separate the urethane products as insolubles and also to neutralize the catalyst.

Urethanes formed by the addition reaction of methyl carbamate and limonene and useful in forming cyclohexyl isocyanates by thermal cracking in accordance with this invention are generally designated by the formulae:

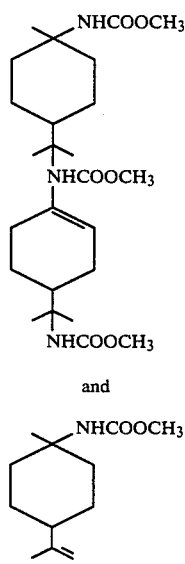

Dipentene urethane esters form the corresponding isocyanate by thermal cracking while splitting off the alkanol. In many cases the alcohol can usefully be recycled by reaction with urea or isocyanic acid (HNCO) to form the starting carbamate ester.

In cracking the urethane esters to form the corresponding isocyanates the catalyst must be removed or neutralized for example, with calcium oxide, sodium carbonate, sodium hydroxide and the like, which is followed by cracking of the urethane ester either solvent free or in high boiling solvents, such as hexadecane, diphenyl ether, diisopropyl naphthalene and the like. Cracking takes place at temperatures on the order of 150° to 350° C. during which the alkanol is split off to yield the corresponding isocyanate.

The mono- and diurethanes obtained by the acid-catalyzed addition reaction of dipentene and methyl urethane can be pyrolyzed or cracked by a batch type method or on a continuous basis under reduced, normal or increased pressure. The cleaving and sparating of the products by distillation of the alcohol, possibly the diisocyanate and any partially reacted monoisocyanate and any unreacted diurethane, and/or optional solvent can take place simultaneously or in a sequence. With simultaneous cleaving and separation in the liquid phase, a temperature-pressure ratio is advantageously chosen which corresponds to the boiling point of the low boiling component of the bottom fraction.

Cracking of dipentene diurethane (DPDU) may be carried out in a batch process without a catalyst at temperatures of 225° to 350° C. without a solvent. Optionally, a catalyst selected from a group of metal oxides may be used, preferably with an inert diluent such as high boiling hydrocarbons or silicones. The reaction is preferably carried out at a temperature of from 225° to 350° C., most preferably at 235°-260° C., at a pressure of from 20 to 50 mm Hg, most preferably at 35-45 mm Hg, in the presence of from 0.1 to 6 wt. percent, most preferably 0.5 to 3 wt. percent of a selective metal oxide catalyst. The reaction time will vary, but usually from about 2 to about 6 hours is sufficient. The progress of the reaction can be followed as a fraction of time, e.g., by means of a gas chromatograph.

It is another object of the invention to provide a process for continuous cracking of dipentene diurethane (DPDU) and/or dipentene monourethane (DPMU) to the desired isocyanates. The urethanes to be cracked are continuously fed through a column packed with inert supports such as glass helices, optionally impregnated or physically mixed with metal oxides catalysts such as CaO, BaO and the like. This results in increased throughput with minimal by-products formation.

The product can be recovered in ways known to those skilled in this art. Distillation is preferred, because it boils at 126°-128° C. under a 2 mm Hg vacuum and at 158°-159° C. under a 15 mm Hg vacuum.

To convert the isocyanates to curable reactants, it is convenient to transform them to vinyl addition polymers or copolymers, e.g., by polymerizing them, alone, or in combination with a reactive co-monomer, such as styrene or ethylene, using free radical or other suitable polymerization conditions well known to those skilled in the art. The resulting polyfunctional isocyanates can then be mixed with a polyhydric compound, with or without solvents, and optionally catalyzed with a tin or other conventional catalyst. The polyhydric compound can comprise a polyol, e.g., trimethylol propane or glycerol, a polyether polyol, e.g., polypropylene glycol, a polyester polyol, e.g., poly(ethylene glycol adipate) a polyamine, e.g., diethylene triamine, a polyamide, or it can comprise water. Conventional functionalities will be selected, e.g, 0.5 to 5 mole of —NCO per mole of —OH, and curing will be effected at 80° to 150° C. during 1 minute to 60 minutes, in the optional presence of 1% by weight of a catalyst, e.g., dibutyl tin dilaurate.

DESCRIPTION OF THE PREFERRED EMBODIMENTS

The following examples illustrate the processes and compounds of the present invention and provide data to show their advantages over the prior art. They are not to be construed to limit the claims in any manner whatsoever.

In the Examples and Tables that follow, the following abbreviations are used:

DP 1-methyl-4-(1-methylethenyl)cyclohexene; limonene; dipentene
MU carbamic acid methyl ester; methyl urethane; methyl carbamate
DPMU dipentene monourethane
DPDU dipentene diurethane
DPDI dipentene diisocyanate

EXAMPLES 1-5

The following general method can be used to produce dipentene diurethanes (DPDU) and dipentene monourethanes (DPMU) from dipentene (DP) and methyl urethane (MU).

Addition reactions were carried out in flasks varying the quantity of MU and the $BF_3 \cdot Et_2O$ catalyst. Reactions were carried out without solvent at 60° C. for 18 hours.

Compositions of the reaction mixtures and results are shown in Table 1.

TABLE I

Addition of Methyl Urethane (MU) to Dipentene (DU) Using $BF_3 \cdot Et_2O$ Catalyst*

| Example | 1 | 2 | 3 | 4 | 5 |
|---|---|---|---|---|---|
| Composition (moles) | | | | | |
| Dipentene (DP) moles | 5.0 | 5.0 | 5.0 | 5.0 | 5.0 |
| Methylurethane (MU) moles | 62 | 31 | 31 | 20 | 20 |
| Boron trifluoride etherate ($BF_3 \cdot Et_2O$) mole | 1.66 | 1.66 | 0.83 | 0.83 | 0.55 |
| $MU/BF_3 \cdot Et_2O$ | 37 | 18.7 | 37 | 24 | 36 |
| eg MU/Olefin (C=C) | 6.2 | 3.1 | 3.1 | 2.0 | 2.0 |
| $BF_3 \cdot Et_2O/DP$ | 0.33 | 0.33 | 0.17 | 0.17 | 0.11 |
| Product Analysis (parts by percentage)$^a$ | | | | | |
| Dienes | 7 | 12 | 21 | 30 | 32 |
| Dipentene Monourethane (DPMU) | 44 | 37 | 34 | 35 | 32 |
| Dipentene Diurethane (DPDU) | 44 | 47 | 43 | 33 | 33 |

*All addition reactions were carried out at 60° C. for 18 hours.

The data in Examples 1 and 5 show that a one-third reduction in catalyst loading ($BF_3 \cdot Et_2O$) increases productivity (DP) by two-fold with only a 10% reduction in DPDU yield. Thus, addition reactions can be run using three times the amount of DP to produce approximately 2.3 times the quantity of DPDU.

EXAMPLE 6

An addition reaction was carried out by following the method of Examples 1-5 with the difference that a solid catalyst, sulfonic acid was substituted for $BF_3 \cdot Et_2O$.

The reaction was carried out in solvent-free methyl urethane (MU) using a 12/1 MU/DP ratio at 62° C. for 18 hours. The sulfonic acid catalyst was Amberlyst-15 ® available from the Rohm & Haas Company. The sulfonic acid catalyst level was about 33 mole percent (%) on the DP charged or approximately 0.5 g Amberlyst ®/g DP (approximately 0.07 g/g total reaction mixture). This level of catalyst is comparable to the levels of $BF_3 \cdot Et_2O$ used in Examples 1 and 2. The reaction was worked up by catalyst filtration, removal of excess MU by aqueous extraction and distillation. Distillation provided the following products analysis: 25% unreacted diene, 55% DPMU and 10% bisurethane (DPDU).

EXAMPLE 7

An addition reaction was carried out following the method of Example 6 except that a polysulfonic acid resin was used in place of the sulfonic acid solid catalyst.

The polysulfonic acid resin employed in this procedure was Nafion-H ® polysulfonic acid resin available from the Du Pont Company.

This reaction mixture gave a slightly higher conversion of DP although yields of the diurethane were somewhat lower than with the sulfonic acid catalyzed reactions.

EXAMPLE 8

DPDU was heated in a batch operation with three times its weight of silicone oil. The silicone oil employed in this procedure was SF 96(−50) ® available from General Electric Company. This resulted in near quantitative conversion to a 90/10 mixture of DPDI and mono-olefin-isocyanate after one hour at a temperature greater than 235° C. While product could be recovered from this DPDI/silicone oil mixture by vacuum stripping, a more desirable alternative was continuous product removal as cracking occurred. This was done by gradually adding a toluene solution of DPDU to a pool of hot silicone oil and continuously sweeping volatile products from the reaction flask on a stream of nitrogen. The oil was maintained at a temperature of 240°-245° C.

EXAMPLE 9

The procedure of Example 8 was followed with the difference that the temperature for cracking was 260°-265° C. instead of 235° C. or greater.

Results indicate that cracking was relatively complete, with 53% DPDI and 20% monoisocyanate-monoolefin along with 10% DPDU and 10% monoisocyanate-monourethane being recovered.

EXAMPLE 10

The procedure of Example 8 was followed except that the DPDU was heated in hexadecane solution instead of silicone oil and at a temperature of 280°-290° C. instead of 235° C. or greater.

Results obtained by this procedure showed that DPDU could be cracked to DPDI to a yield of approximately 90%.

EXAMPLE 11

A vertical tube reactor, electrically heated is packed with glass helices. This is heated to 310°-325° C. and, at atmospheric pressure, a solution of 20 percent by weight of dipentene diurethane is fed into the top of the reactor at a rate of 2 g. of urethane per hour. Nitrogen is used to sweep the flow downward, and a cooled receiver at the bottom is employed to collect the products. The corresponding dipentene diisocyanate is obtained in good yield with greater than 90 percent material recovery. When the corresponding monourethanes are substituted, high yields of the corresponding monoisocyanates are also obtained in this continuous process.

EXAMPLE 12

The procedure of Example 11 was repeated with glass helices coated with powdered calcium oxide. Again, high yields of the isocyanates were obtained with over 90 percent material recovery at a feed rate of 2 g. per hour of urethane.

EXAMPLE 13

The procedure was repeated with a mixture of granular calcium oxide and glass helices in the heated reaction zone. Substantially the same results were obtained.

EXAMPLE 14

A curable composition is prepared by reacting a hydrocarbon solvent solution comprising equal molar amounts of the diisocyanate of Example 9, DPDI, and ethylene, catalyzed with 0.5 percent by weight of azobisisobutyronitrile, at 80° C. for 16 hours. Evaporation of the solvent will leave a copolymer of DPDI and ethylene as a residue. This will cure on exposure to moisture to a composition utility as an adhesive or as a protective film.

If the composition is mixed in a solvent with trimethylol propane, or with diethylene triamine, at an —NCO/—OH ratio of 1.1:1, using 1% by weight of tin (TRS), upon evaporation of the solvent and heating at 100° C. for 20 minutes, a solvent resistant hard film should be obtained.

The above-mentioned patents and publications are incorporated by reference.

Many variations will suggest themselves to those skilled in the art in light of the above, detailed description. For example, instead of using the methyl ester of carbamic acid in the addition reaction, the ethyl, propyl, butyl, triacontyl or any of the higher alkyl esters of carbamic acid can be used. Instead of boron trifloride etherate or the sulfonic acid ion exchange resin, other catalysts such as concentrated sulfuric acid, can be employed.

All such obvious variations are within the full intended scope of the appended claims.

We claim:

1. A compound having the formula

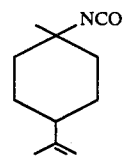 (V)

2. A compound as defined in claim 1 further comprising a compound having the formula

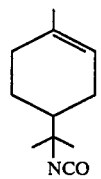 (IV)

* * * * *